(12) United States Patent
Parker

(10) Patent No.: US 7,686,839 B2
(45) Date of Patent: Mar. 30, 2010

(54) PHOTOTHERAPY TREATMENT DEVICES FOR APPLYING AREA LIGHTING TO A WOUND

(75) Inventor: Jeffery R. Parker, Richfield, OH (US)

(73) Assignee: Lumitex, Inc., Strongsville, OH (US)

( * ) Notice: Subject to any disclaimer, the term of this patent is extended or adjusted under 35 U.S.C. 154(b) by 377 days.

(21) Appl. No.: 11/043,874

(22) Filed: Jan. 26, 2005

(65) Prior Publication Data

US 2006/0167532 A1    Jul. 27, 2006

(51) Int. Cl.
  *A61N 5/06*    (2006.01)
(52) U.S. Cl. .......................................... 607/93; 607/88
(58) Field of Classification Search ............. 607/88–94; 362/600–620
  See application file for complete search history.

(56) References Cited

U.S. PATENT DOCUMENTS

| | | | |
|---|---|---|---|
| 4,234,907 A * | 11/1980 | Daniel .......................... | 362/556 |
| 4,547,040 A * | 10/1985 | Yamamoto et al. .......... | 385/143 |
| 4,761,047 A | 8/1988 | Mori | |
| 4,907,132 A * | 3/1990 | Parker .......................... | 362/556 |
| 5,005,108 A | 4/1991 | Pristash et al. | |
| 5,042,900 A * | 8/1991 | Parker .......................... | 385/76 |
| 5,097,396 A | 3/1992 | Myers | |
| 5,136,480 A * | 8/1992 | Pristash et al. .............. | 362/618 |
| 5,226,105 A | 7/1993 | Myers | |
| 5,295,216 A | 3/1994 | Halter | |
| 5,301,090 A * | 4/1994 | Hed ............................. | 362/558 |
| 5,303,323 A | 4/1994 | Mezei | |
| 5,432,876 A * | 7/1995 | Appeldorn et al. .......... | 385/31 |
| 5,445,608 A * | 8/1995 | Chen et al. .................. | 604/20 |
| 5,474,528 A * | 12/1995 | Meserol ....................... | 604/20 |
| 5,568,964 A * | 10/1996 | Parker et al. ................ | 362/556 |
| 5,613,751 A | 3/1997 | Parker et al. | |
| 5,616,140 A * | 4/1997 | Prescott ....................... | 606/10 |
| 5,913,245 A * | 6/1999 | Grossman .................... | 73/800 |
| 5,944,748 A * | 8/1999 | Mager et al. ................. | 607/88 |
| 6,045,575 A | 4/2000 | Rosen et al. | |
| 6,267,779 B1 * | 7/2001 | Gerdes ......................... | 607/89 |
| 6,290,713 B1 | 9/2001 | Russell | |
| 6,350,275 B1 | 2/2002 | Vreman et al. | |
| 6,443,978 B1 * | 9/2002 | Zharov ........................ | 607/91 |
| 6,596,016 B1 | 7/2003 | Vreman et al. | |
| 6,641,601 B1 | 11/2003 | Augustine et al. | |
| 6,730,113 B2 * | 5/2004 | Eckhardt et al. ............. | 607/94 |
| 6,743,249 B1 * | 6/2004 | Alden .......................... | 607/88 |
| 6,811,563 B2 * | 11/2004 | Savage et al. ............... | 607/88 |
| 6,830,580 B2 * | 12/2004 | Neuberger .................... | 607/89 |
| 6,872,220 B2 | 3/2005 | Williams et al. | |
| 6,989,023 B2 * | 1/2006 | Black .......................... | 607/90 |
| 7,001,413 B2 * | 2/2006 | Butler .......................... | 607/88 |
| 2002/0138120 A1 * | 9/2002 | Whitehurst .................. | 607/88 |
| 2002/0143373 A1 * | 10/2002 | Courtnage et al. ........... | 607/91 |
| 2003/0009205 A1 * | 1/2003 | Biel ............................. | 607/88 |
| 2003/0114902 A1 * | 6/2003 | Prescott ........................ | 607/89 |

(Continued)

*Primary Examiner*—Henry M Johnson, III
(74) *Attorney, Agent, or Firm*—Renner, Otto, Boisselle & Sklar, LLP

(57) ABSTRACT

Phototherapy treatment devices include a light emitter that is adapted to be placed in close proximity to a wound for applying light/heat energy to the wound to aid in the healing process. The light emitter may comprise a light guide that receives light from a light source or a light source that is affixed to a substrate used to position the light source over the wound.

16 Claims, 3 Drawing Sheets

U.S. PATENT DOCUMENTS

| | | | |
|---|---|---|---|
| 2003/0167080 A1* | 9/2003 | Hart et al. | 607/88 |
| 2003/0202338 A1* | 10/2003 | Parker | 362/31 |
| 2004/0008523 A1* | 1/2004 | Butler | 362/551 |
| 2004/0068305 A1* | 4/2004 | Bansal et al. | 607/89 |
| 2004/0078068 A1* | 4/2004 | Neuberger | 607/88 |
| 2004/0120684 A1* | 6/2004 | Ishibashi et al. | 385/141 |
| 2004/0127961 A1* | 7/2004 | Whitehurst | 607/88 |
| 2005/0070976 A1 | 3/2005 | Samuel et al. | |
| 2005/0075703 A1* | 4/2005 | Larsen | 607/88 |
| 2005/0137656 A1* | 6/2005 | Malak | 607/88 |
| 2005/0149150 A1* | 7/2005 | McDaniel | 607/88 |
| 2005/0288746 A1* | 12/2005 | Perez | 607/88 |
| 2007/0029523 A1* | 2/2007 | Ishibashi et al. | 252/301.36 |
| 2007/0060984 A1* | 3/2007 | Webb et al. | 607/89 |

\* cited by examiner

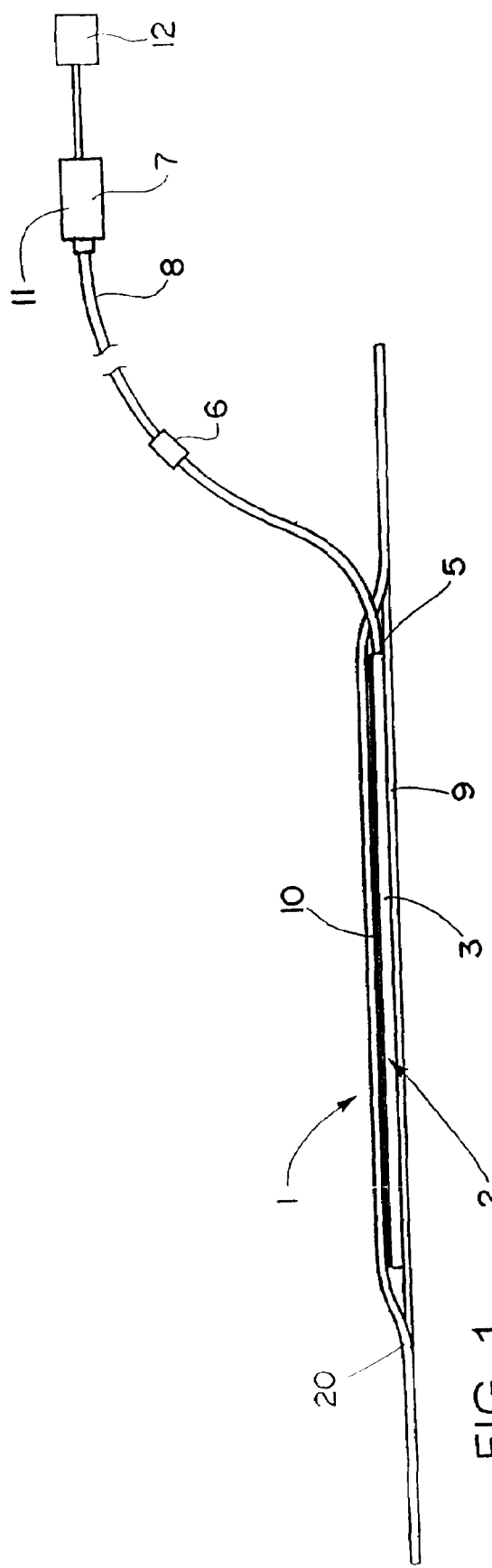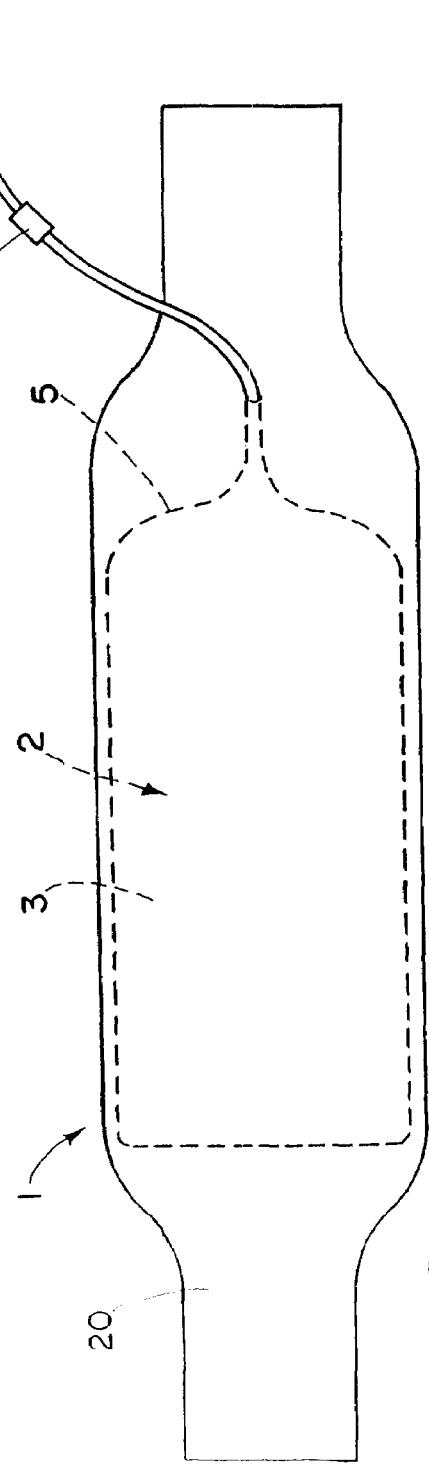
FIG. 1
FIG. 2

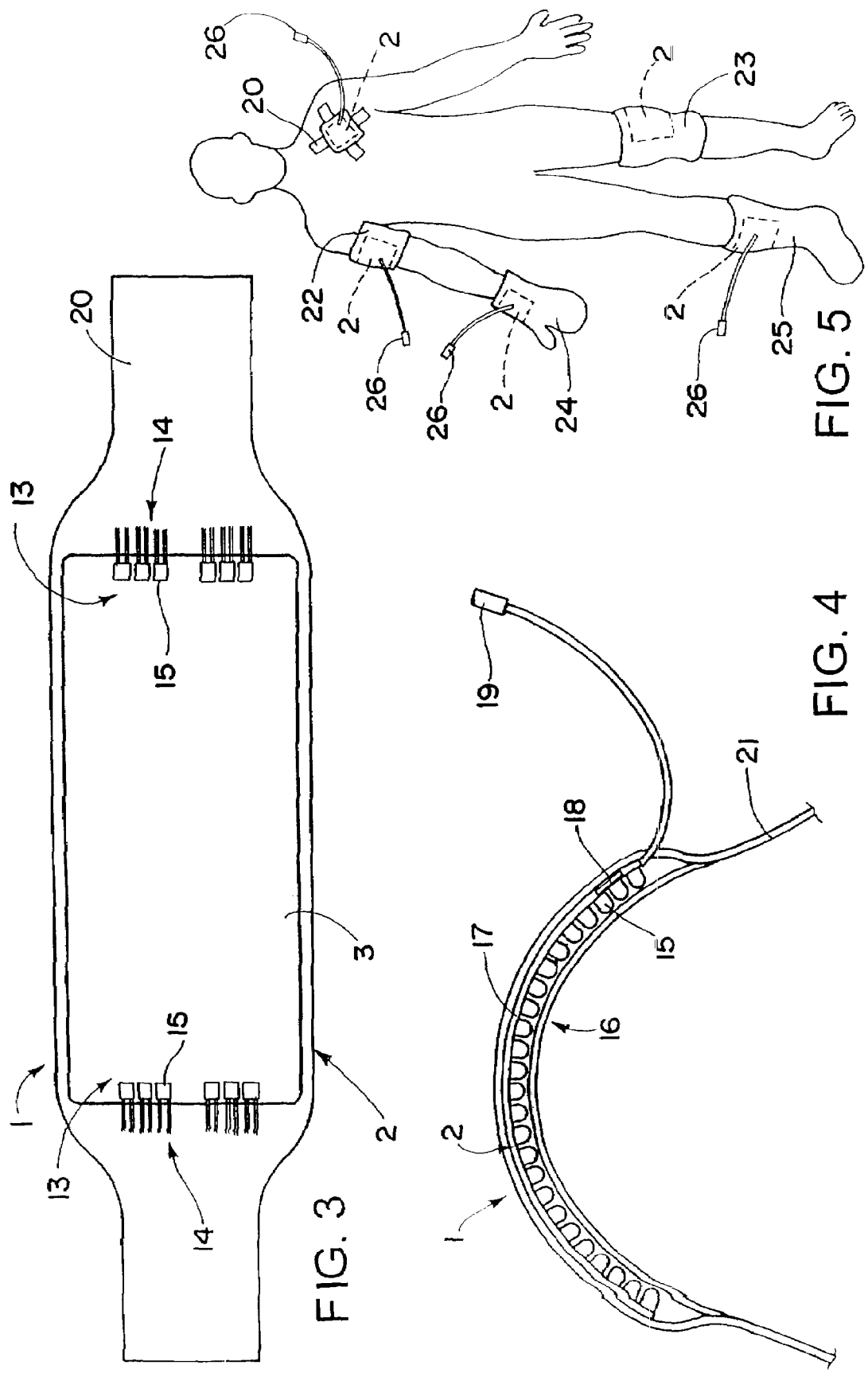

_US 7,686,839 B2_

PHOTOTHERAPY TREATMENT DEVICES FOR APPLYING AREA LIGHTING TO A WOUND

FIELD OF THE INVENTION

This invention relates to phototherapy treatment devices for use in applying area light energy to a wound to help in the healing process.

BACKGROUND OF THE INVENTION

Phototherapy has long been used to treat various medical conditions including, for example, jaundice in newborn infants. Jaundice is caused by a build up of bilirubin in the blood of infants. Exposing the infant's skin to certain types of light will reduce the bilirubin to a safe level.

Phototherapy has also long been used to help treat various other medical conditions, with varying degrees of success. Heretofore a major drawback in using previous phototherapy devices was their inability effectively to control the amount, type and/or extent of light energy to different areas of the body of an individual, particularly for prolonged periods of time, with minimal inconvenience to the individual.

SUMMARY OF THE INVENTION

The phototherapy treatment devices of the present invention include a light emitter that is positioned in close proximity to a wound for applying light energy to the wound to aid in the healing process.

In accordance with one aspect of the invention, the light emitter is sized and shaped to emit light substantially only over the entire surface area of the wound.

In accordance with another aspect of the invention, the light emitter may comprise a light guide having a greater width and length than thickness that receives light from a light source and causes the light to be reflected or refracted out of the light guide toward the wound. The light guide may be rigid or flexible, and may comprise a polymer light guide or a plurality of optical fibers that emit light toward the wound. Also the optical fibers may be of different lengths and emit light at their ends toward the wound.

In accordance with another aspect of the invention, the light emitter may comprise a light source that is affixed to a substrate used to position the light source over the wound.

In accordance with another aspect of the invention, the light source may comprise an array of light emitting diodes affixed to the substrate.

In accordance with another aspect of the invention, suitable positioning means may be used for positioning the area light emitter in overlying relation to the wound, including for example an adhesive patch or tape, or a strap or band such as a wrist, arm, leg, or knee band. Alternatively the light emitter may be contained in a garment such as a mitten, glove, hat, cap, arm or leg banding or other article of clothing for positioning the light emitter in close proximity to the wound. Also the positioning means may serve another medical function or purpose. For example the positioning means may be a cast, splint, band, wrap or other device that also serves a medical purpose.

In accordance with another aspect of the invention, the light energy that is emitted from the light emitter may be infrared radiation, ultraviolet radiation, visible radiation or other predetermined frequencies, bandwidths or colors of light. Ultraviolet light may also be emitted for infection control to kill surface bacteria in a wound. Also the light energy that is emitted may be used to activate, excite, or act as a catalyst for another substance during phototherapy treatment.

In accordance with another aspect of the invention, the light energy that is emitted from the light emitter may be pulsed to allow greater light intensities to be used to penetrate the wound to a greater depth or to reduce cumulative heat build up.

These and other objects, advantages, features and aspects of the invention will become apparent as the following description proceeds.

To the accomplishment of the foregoing and related ends, the invention, then, comprises the features hereinafter more fully described and particularly pointed out in the claims, the following description and the annexed drawings setting forth in detail certain illustrative embodiments of the invention, these being indicative, however, of but several of the various ways in which the principles of the invention may be employed.

BRIEF DESCRIPTION OF THE DRAWINGS

In the annexed drawings:

FIG. 1 is a schematic side elevation view of one form of phototherapy treatment device in accordance with this invention;

FIG. 2 is a schematic top plan view of the phototherapy treatment device of FIG. 1;

FIG. 3 is a schematic bottom plan view of another form of phototherapy treatment device of the present invention;

FIG. 4 is a schematic side elevation view of still another form of phototherapy treatment device of the present invention; and FIG. 5 is a schematic illustration showing various ways in which the phototherapy treatment devices of the present invention may be applied to wounds to different body parts of an individual.

DETAILED DESCRIPTION OF THE INVENTION

Referring now in detail to the drawings, wherein like reference numbers are used to designate like parts, and initially to FIGS. 1 and 2, there is shown one form of phototherapy treatment device 1 in accordance with this invention including an area light emitter 2 that may be sized and shaped to substantially only cover the entire surface area of a wound or other area of a person's body for applying light energy substantially only to the wound or other body area to produce light energy to aid in the healing process. In the embodiment shown in FIGS. 1 and 2, the light emitter 2 is in the general shape of a relatively thin light guide 3 having a greater length and width than thickness and opposite sides and ends and side edges, giving the light emitter increased flexibility.

Figure 2A:
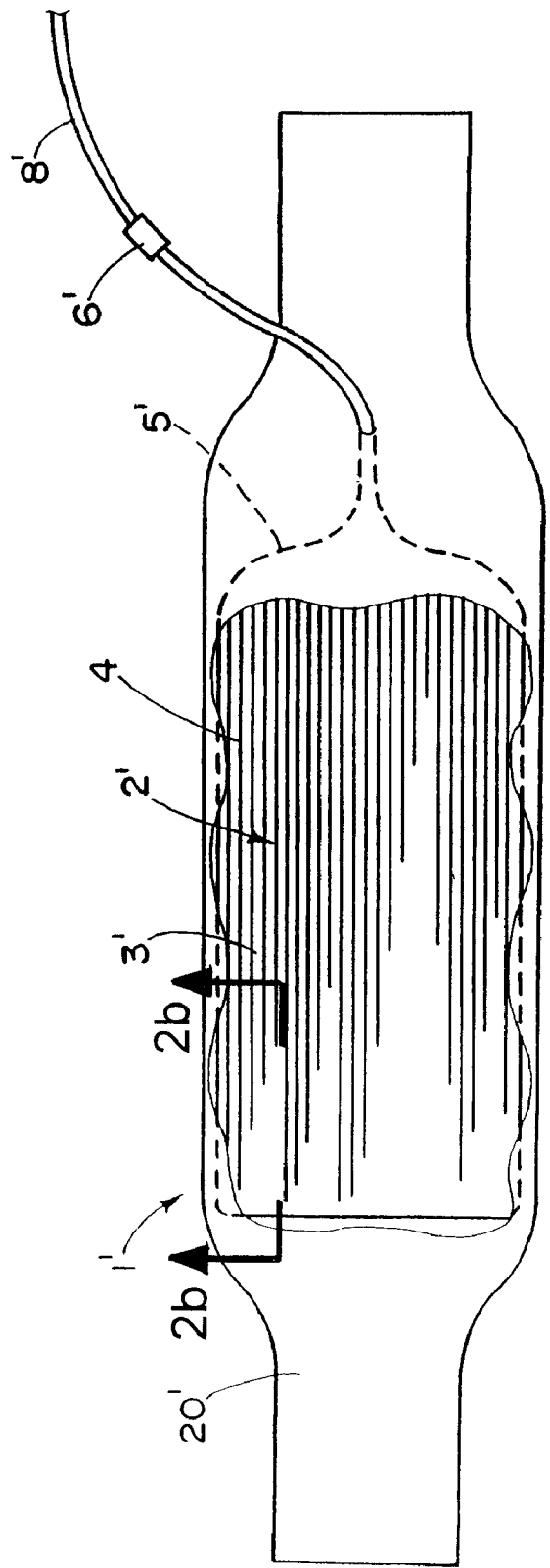
FIG. 2a is a schematic top plan view of another form of phototherapy treatment device of the present invention.
Figure 2B:
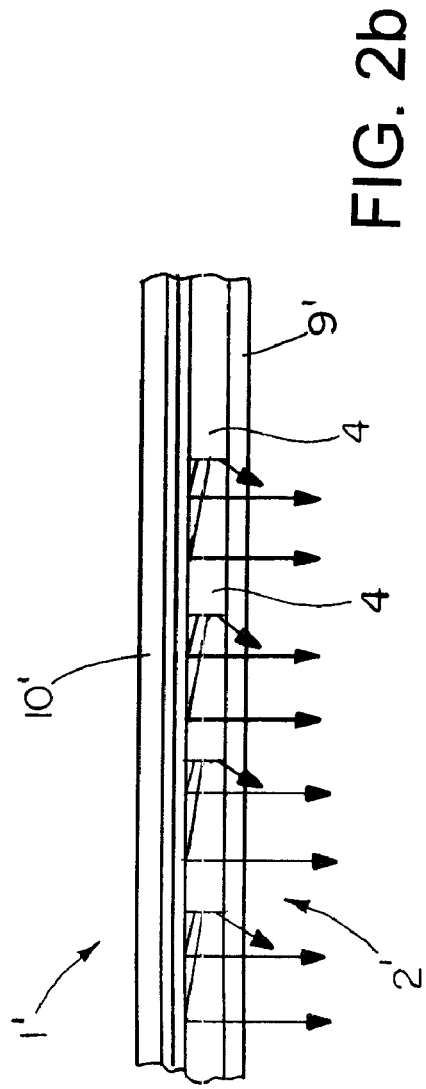
FIG. 2b is an enlarged fragmentary longitudinal section through the phototherapy treatment device of FIG. 2a taken generally on the plane of the line 2b-2b thereof.

Attached to one end 5 of the light guide is a connector 6 for connection of the light guide to a light source 7 via a light cable 8. To cause light to be emitted from the light guide, one or both sides of the light guide may be disrupted as by marring, abrading, scratching or otherwise causing mechanical, chemical or other disruptions at discrete locations along the length of the light guide. The amount of light emitted at these locations will depend on the depth, size and/or frequency of such disruptions. For example, if the disruptions are made larger and/or deeper and/or closer together as the distance from the light receiving end 5 of the light guide 3 increases, there will be more uniform emission of light from the light guide. Also if desired, where the light guide is comprised of optical fibers, the optical fibers 4 may be of different lengths over the length and width of the light guide 3' as schematically shown in FIGS. 2a and 2b to cause light to be emitted from the ends 4' of the optical fibers and reflected toward the wound in a pinpoint pattern at different points over the length and width of the light guide.

The light guide 3 may either be a solid optically transparent polymer light guide or comprised of a plurality of optical fibers as desired, and includes a light emitting surface 9 on one side that is larger than the cross sectional area of the light cable to reduce energy density by spreading the light over a larger surface area at the light emitting surface. Also the light guide may be molded, formed or shaped to fit a particular application.

A suitable back reflector 10 made, for example, of Mylar or other suitable light reflective material, may be applied to the other side of the light guide for reflecting any light directed toward the other side back out the light emitting surface 9 toward the wound or other body area to be treated with phototherapy.

Light source 7 may comprise a light generator 11 for generating different frequencies, bandwidths and/or colors of light including infrared radiation, ultraviolet radiation, and/or visible radiation. Ultraviolet radiation may be used for infection control to kill surface bacteria in a wound.

A switch or controller 12 of any suitable type may be provided for causing the light generator 11 to be switched between the different frequencies, bandwidths and/or colors of light generated thereby to suit a particular application. For example, where the wound is internal, specific wavelengths of light may be used to penetrate deeper into tissue to penetrate the internal wound. Also the controller may be used to cause the light that is emitted by the light emitter to be pulsed to allow greater light intensities to be used to penetrate the wound or other body area to a greater depth and/or to reduce cumulative heat build up in the wound. Further, the light energy emitted from the light emitter may be used to activate, excite or act as a catalyst for another substance during phototherapy treatment. A filter (not shown) may also be interposed between the light source 7 and light emitter 2 to filter out any undesired frequencies of light.

Where the light guide 3 is a solid optically transparent light guide, the light guide 3 may have one or more light transition areas (mixing areas) 13 adjacent one or both ends of the light guide containing a plurality of light sources 14 at one or both ends of the light guide as shown in FIG. 3. Each transition area mixes the light from one or more light sources having different colors and/or intensities. In this particular embodiment, each of the light sources 3 may employ three different colored light emitting diodes 15 (red, blue and green) in each transition mixing area 13 so that the light from the three light emitting diodes (LEDs) can be mixed to produce virtually any desired colored light output or white light output distribution to suit a particular application.

In another form of the invention shown in FIG. 4, the area light emitter 2 may comprise a light source 16 affixed to a suitable substrate 17 sized and shaped to position the light source for emitting light substantially only over the entire surface area of a wound or other body area. In this embodiment, the light source 16 may comprise an array of low wattage LEDs 15 (including organic light emitting diodes and/or poly light emitting diodes), which may be on a flexible circuit. The actual number of LEDs within a given light source may vary depending on the particular wattage output of the LEDs and the amount of light output to be emitted from the light emitter per unit light emitting surface area. The assembly may be encapsulated, coated, covered or sealed to insulate the electronics and/or protect against moisture. This also allows for easier sterilization of the device. If a covering is used, the covering may be resterilizable or disposable as desired.

Regardless of the type of light source 7, 14 or 16 used, the light source may be powered by a battery or fuel cell 18 (see FIG. 4) for ease of portability or provided with an electrical plug 19 for connection to an electrical outlet. In any case, various means may be used for positioning the light emitter 2 in overlying relation to a wound or other body area including for example an adhesive patch or tape 20 as shown in FIGS. 1-3 and 5 or a strap or band 21 such as a wrist or arm band 22 or knee or leg band 23 as shown in FIGS. 4 and 5. Alternatively, the light emitter 2 may be contained in a mitten or glove 24 as shown in FIG. 5 or other type of garment including a hat, cap or other article of clothing. Further the positioning means may also serve another medical function or purpose. For example, the positioning means may be a cast, splint, bandage, wrap or other device that serves another medical purpose. FIG. 5 shows one such example in which the light emitter 2 is contained in a cast 25 that is casted around a body part of an individual such as a leg or foot.

In any case, the light emitter 2 and means for positioning may either be disposable or reusable depending on the particular application. Also the means for positioning may include an internal light source 15 and/or power source 18 (as for example in the case of the knee or leg band 23 shown in FIG. 5), or may have a connector 26 connected thereto (as in the case of the patch 20, band or strap 22, mitten or glove 24 and cast 25 shown in FIG. 5) either to permit an internal light guide 3 such as shown in FIGS. 1 and 2 to be connected to a remote light source 7 or an internal light source 14 or 15 such as shown in FIGS. 3 and 4 to be connected to an external power supply.

From the foregoing, it will be apparent that the phototherapy treatment devices of the present invention provide an effective means for applying area light energy to specific areas of the body during phototherapy treatment to help heal surface wounds or cuts as well as internal wounds such as broken bones or ligament damage and the like. Also the area light energy that is applied by such phototherapy treatment devices to different areas of the body may be used for other types of phototherapy treatment as well including, among others, infection control to kill surface bacteria in a wound, or to activate, excite or act as a catalyst for other substances. For example, in photodynamic therapy cancer treatment, the phototherapy treatment devices of the present invention may be used to supply specific wavelengths of light to different areas of the body to activate known photosensitizing agents injected into the body to kill nearby cancer cells.

Although the invention has been shown and described with respect to certain embodiments, it is obvious that equivalent alterations and modifications will occur to others skilled in the art upon the reading and understanding of the specification. In particular, with regard to the various functions performed by the above-described components, the terms (including any reference to a "means") used to describe such components are intended to correspond, unless otherwise indicated, to any component which performs the specified function of the described component (e.g., that is functionally equivalent) even though not structurally equivalent to the disclosed component which performs the functions in the herein exemplary embodiments of the invention. In addition, while a particular feature of the invention may have been disclosed with respect to only one embodiment, such feature may be combined with one or more other features of other embodiments as may be desired or advantageous for any given or particular application.

What is claimed is:

1. A phototherapy treatment device comprising an area light emitter, means for positioning the light emitter in close proximity to a wound of a patient, and means for causing light to be emitted from the light emitter towards the wound for applying light energy to the wound, wherein the light emitter comprises a light guide that receives light from a light source and causes light to be reflected or refracted out of the light guide toward the wound, the light guide including a plurality of optical fibers of different lengths terminating at respective ends at different locations over the length and width of the light guide to cause light to be emitted from the ends of the optical fibers and reflected toward the wound in a pinpoint pattern at different points over the length and width of the light guide.

2. The device of claim 1 wherein the light energy produces heat to help heal the wound.

3. The device of claim 1 further comprising a connector for connecting the light guide to the light source.

4. The device of claim 1 wherein the light guide is flexible.

5. The device of claim 1 wherein the light emitter is encapsulated, coated, covered or sealed.

6. The device of claim 1 wherein the means for positioning comprises an adhesive patch or tape for attaching the light emitter in overlying relation to the wound.

7. The device of claim 1 wherein the means for positioning comprises a band or strap to which the light emitter is attached.

8. The device of claim 1 wherein the means for positioning comprises a garment that is used to hold the light emitter in overlying relation to the wound.

9. The device of claim 1 wherein the light emitted from the light emitter is at least one of the following: infrared radiation, ultraviolet radiation, or visible radiation.

10. The device of claim 1 wherein the light emitted from the light emitter is ultraviolet light for infection control to kill surface bacteria in the wound.

11. The device of claim 1 further comprising means for selectively changing the color or predetermined frequency or bandwidth of light energy emitted from the light emitter.

12. The device of claim 1 wherein the means for positioning comprises an immobilizing cast or splint that is worn by the patient to serve a medical function or purpose.

13. The device of claim 1 further comprising a controller means for controlling the amount of light energy emitted from the light emitter.

14. The device of claim 13 wherein the controller means includes means for pulsing the light energy emitted from the light emitter to allow greater light intensities to be used to penetrate the wound to a greater depth.

15. The device of claim 13 wherein the controller means includes means for pulsing the light energy emitted from the light emitter to reduce cumulative heat buildup.

16. A phototherapy treatment device comprising an area light emitter, means for positioning the light emitter in close proximity to a wound of a patient, and means for causing light to be emitted from the light emitter towards the wound for applying light energy to the wound, wherein the light emitter comprises a light guide that receives light from a light source and causes light to be reflected or refracted out of the light guide toward the wound, wherein the light guide has a greater width and length than thickness, and wherein the light guide comprises a plurality of optical fibers of different lengths terminating at respective ends at different locations over the length and width of the light guide to cause light to be emitted from the ends and reflected toward the wound in a pinpoint pattern over the length and width of the light guide.

* * * * *